(12) United States Patent  (10) Patent No.: US 6,976,584 B2
Maiola et al.  (45) Date of Patent: Dec. 20, 2005

(54) PACKAGE FOR SURGICAL IMPLANT

(75) Inventors: Anthony Walter Maiola, Rochester, NY (US); Matthew Scott Jonasse, Sodus, NY (US)

(73) Assignee: Bausch & Lomb Incorporated, Rochester, NY (US)

( * ) Notice: Subject to any disclaimer, the term of this patent is extended or adjusted under 35 U.S.C. 154(b) by 178 days.

(21) Appl. No.: 10/183,804

(22) Filed: Jun. 26, 2002

(65) Prior Publication Data

US 2004/0000499 A1 Jan. 1, 2004

(51) Int. Cl.[7] .............................................. B65D 85/00
(52) U.S. Cl. ...................... 206/438; 206/5.1; 220/359.2
(58) Field of Search ...................... 206/5.1, 339, 438, 206/480, 481, 570–572; 220/359.1–359.2; 606/107; 623/5.11, 5.12

(56) References Cited

U.S. PATENT DOCUMENTS

| 4,497,406 A | * | 2/1985 | Takanashi | 206/438 |
| 4,736,836 A | | 4/1988 | Alongi et al. | 206/5.1 |
| 5,378,475 A | | 1/1995 | Smith et al. | 424/473 |
| 5,565,228 A | * | 10/1996 | Gics | 426/107 |
| 5,669,501 A | | 9/1997 | Hissong et al. | 206/438 |
| 5,773,019 A | | 6/1998 | Ashton et al. | 424/423 |
| 5,823,327 A | * | 10/1998 | Wu et al. | 206/5.1 |
| 5,941,390 A | | 8/1999 | Franceschi et al. | 206/438 |
| 6,001,386 A | | 12/1999 | Ashton et al. | 424/423 |
| 6,217,895 B1 | | 4/2001 | Guo et al. | 424/427 |
| 6,375,972 B1 | | 4/2002 | Guo et al. | 424/423 |
| 2003/0034267 A1 | * | 2/2003 | De Luca et al. | 206/438 |

FOREIGN PATENT DOCUMENTS

| EP | 0250904 | 6/1987 |
| WO | WO 02/39946 | 5/2002 |

* cited by examiner

Primary Examiner—Jim Foster
(74) Attorney, Agent, or Firm—Glenn D. Smith

(57) ABSTRACT

A package for storing an implantable medical device during storage and shipping includes a containment region for containing the device, a flange surrounding the containment region, and lidstock sealed against this flange. A recess in the containment region permits insertion of a surgical gripping tool below the device support surface. The package may further include ribs that facilitate steadying or gripping the package during removal of the lidstock, and a separate receptacle for holding the device after removal from the containment region. The device is preferably a device implantable in the human eye.

3 Claims, 4 Drawing Sheets

PACKAGE FOR SURGICAL IMPLANT

BACKGROUND OF THE INVENTION

This invention relates to a package for containing a surgical implantable device, particularly an ophthalmic device for implanting in the human eye. Various devices for implanting in the eye are known. As examples, devices for sustained delivery release of a pharmaceutically active ingredient into the back-of-the-eye are disclosed in the following patents, the disclosures of which are incorporated herein by reference: U.S. Pat. No. 6,375,972; U.S. Pat. No. 5,773,019; U.S. Pat. No. 5,378,475; U.S. Pat. No. 6,001,386; and U.S. Pat. No. 6,217,895.

SUMMARY OF THE INVENTION

Figure 1:
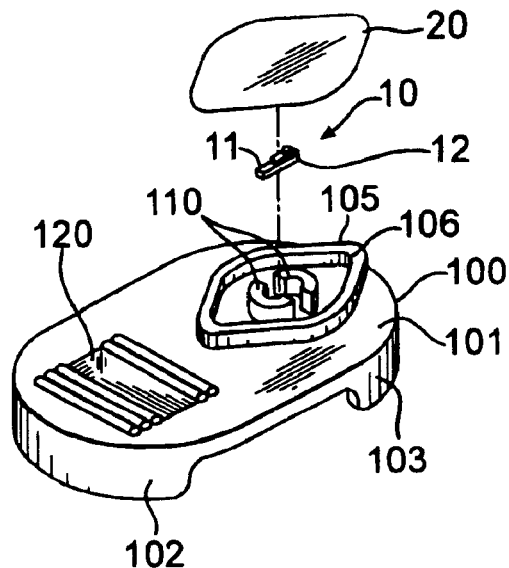
FIG. 1 is an exploded top perspective view of a package according to various preferred embodiments of this invention, including a medical device and lidstock.
Figure 2:
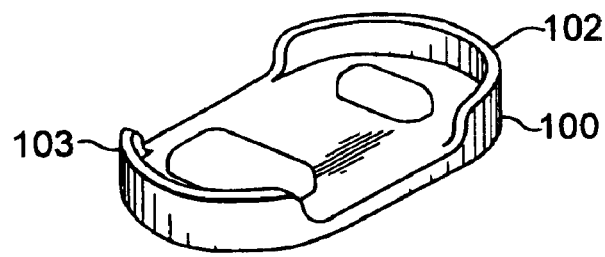
FIG. 2 is a bottom schematic perspective view of the package shown in FIG. 1.
Figure 3:
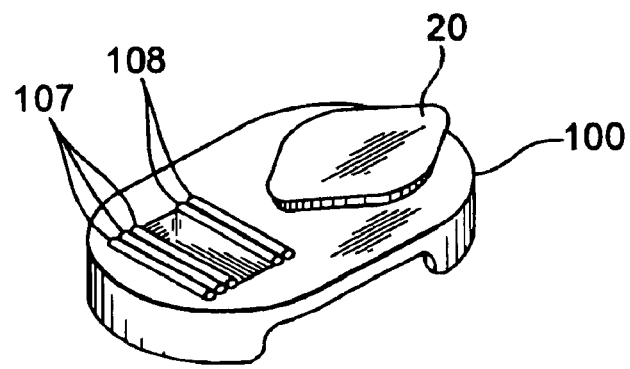
FIG. 3 is a top perspective view of the package of FIG. 1 including lidstock.
Figure 4:
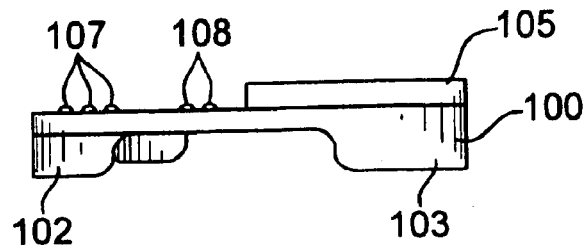
FIG. 4 is side view of the package of FIG. 1.

This invention provides a package for storing an implantable medical device during storage and shipping. The package comprises a first flange extending upwardly from an upper surface and defining a containment region for containing the device, wherein the containment region includes a support surface for supporting the device in the containment region. The package further comprises a second flange extending upwardly from the upper surface, wherein the second flange completely surrounds the first flange and includes an upper surface for sealing of lidstock thereto.

According to preferred embodiments, the package comprises a recess extending below the device support surface in the containment region, such that the recess permits insertion of a surgical gripping tool below this device support surface. The first flange may have the form of two protrusions extending upwardly from the package upper surface and defining the containment region, for example, the recess may then have the form of an elongated groove in the package upper surface that separates the two protrusions and extends transversely to the containment region. Preferably, these two protrusions are both arcuate.

The package may further include ribs that facilitate steadying or gripping the package during removal of the lidstock. The ribs may extend upwardly from the same upper surface from which the second flange extends, or the ribs may extend from a second package upper surface at a different elevation than the first package upper surface.

According to preferred embodiments, the package includes a holding receptacle for holding the device after removal from the containment region. For example, the holding receptacle may have the form of a groove formed in the package upper surface and located between the ribs.

The device is preferably a device implantable in the human eye, wherein the containment region is sized to contain such a device while preventing excessive movement of the device during storage and shipping. Accordingly, the containment region preferably has a maximum length of 10 mm. For packages including two first flange protrusions, the maximum length between inner surfaces of the two protrusions is 10 mm, and the maximum width between inner surfaces of an individual protrusion is 10 mm, more preferably 5 mm.

DETAILED DESCRIPTION OF PREFERRED EMBODIMENTS

FIGS. 1 to 6 illustrate a package 100 according to various preferred embodiments. Package 100 includes a top planar surface 101 with front and rear vertical sidewalls 102, 103 extending downwardly from planar surface 101 and serving to support the package on a work surface.

The package is designed to contain a sterile device 10 during shipping and storage, wherein sterility of the device is maintained and the device is protected from damage. Outer flange 105 extends upwardly from planar surface 101. For the embodiment shown in FIGS. 1 to 6, flange 105 is generally diamond-shaped with rounded corners. Flange 105 includes an upper surface 106. After placing device 10 in the package, lidstock 20 is hermetically sealed against surface 106, so that the package assembly assumes the configuration shown in FIG. 3. Surface 106 may be flat or arcuate. The lidstock 20 may be hermetically sealed against surface 106 by conventional heat sealing. Representative materials for lidstock 20 include vapor and moisture impermeable materials such as plastics or metallic laminates. Lidstock 20 will generally be slightly larger than the outer perimeter of flange 106 so that portions of the lidstock overhand flange 106. Such overhanging portions of lidstock 20 allow a user to grip the overhanging portion when removing the lidstock 20 to access the device. An advantage of the diamond-shaped flange 106 in FIGS. 1 to 6 is that the lidstock may be pulled from multiple points, i.e., from each corner of the flange, depending on the preference of the user. The embodiment shown in FIGS. 1 to 6 includes ribs 107, 108 protruding upwardly from surface 101. A user may place a thumb or fingers on these ribs while removing lidstock 20 with the other hand in order to steady the package on a support surface.

Figure 11:
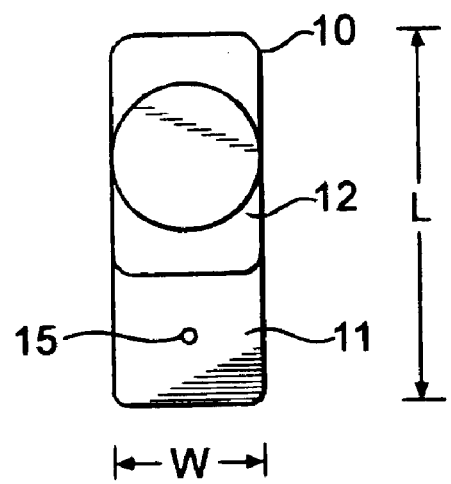
FIG. 11 is a top view of a medical device shown in FIG. 1.
Figure 12:
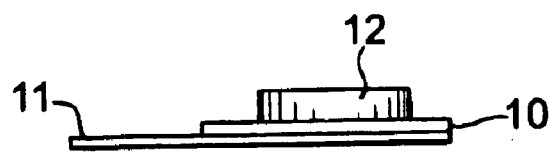
FIG. 12 is a side view of the device of FIG. 11.

Package 10 includes inner flanges 110, protruding upwardly from surface 110 and contained inside the boundary defined by outer flange 106, serving to closely contain device 10 while stored in the container. In other words, inner flanges 110 form a containment region and prevent device 10 from moving excessively during shipping and storage, thus minimizing the risk of damaging device 10. Also, inner flanges 110 ensure that the device 10 is presented in a predetermined configuration after removing the lidstock 20 from the package, this configuration best seen in FIG. 5. For the illustrated embodiment, flanges 110 are arcuately shaped. A representative device 10 is illustrated in FIGS. 11 and 12. For the illustrated embodiment, device 10 has a sustained release portion 12 in which a drug is encased, and a suture tab portion including a suture hole 15. The length of the device is indicated by "L" and the width of the device is indicated by "W". It is preferred that the maximum length of the containment region bounded by the inner surfaces of the two flanges 110 is no greater than 2.5 mm of the length of the device (more preferably no greater than 2 mm), and/or the maximum width of this containment region bounded with the inner surfaces of each flange 110 is no greater than 2.5 mm of the width of the device (more preferably no greater than 2 mm), in order to protect the device from excessive movement. It is further preferred that at least one of the length and width is no greater than 1 mm than the respective length or width of the implant device. As an example, for a device implantable in the eye having a length of about 5.3 mm, the maximum length of the containment region between the inner surfaces of the two flanges 110 should be no greater than 7.8 mm (7.2 mm being suitable); for such a device having a width of about 2.0 mm, the maximum width of the containment region between the inner surfaces of an individual flange 110 should be no greater than 4.5 mm (2.8 mm being suitable). If desired, the lidstock 20 may be also sealed against upper surfaces of inner flanges 110.

In this embodiment, package 100 includes a recess 112 extending downwardly from surface 110, contained inside the boundary defined by outer flange 106 and extending between inner flanges 110. In other words, device 10 rests on a pair of surfaces defining device support surface 115, best seen in FIG. 6, bounded within flanges 110. In removing the device 10 from the package, a surgeon will typically grip the device with tweezers or another type of surgical gripping tool. Recess 112 permits the surgeon to insert the tweezers or tool below the device and device support surface 115 on which the device rests. Stated differently, the surgeon is not required to grip the device with the very tip of the tweezers or tool. In contrast, in various other packages for small medical devices, the devices rest entirely on a flat or concave surface, requiring the surgeon to access the device with the tool tip. It has been found that providing access below the device is less awkward and facilitates easier removal and handling. In the illustrated embodiment, recess 112 is an elongated groove extending transversely to device support surfaces 115 and separating inner flanges 110 from each other.

Figure 5:
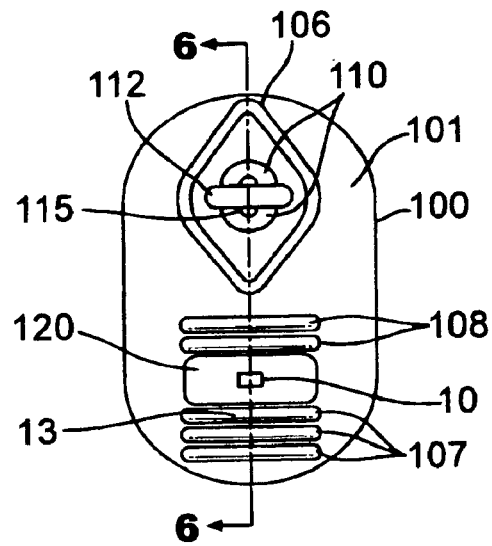
FIG. 5 is a top view of the package of FIG. 1.
Figure 6:
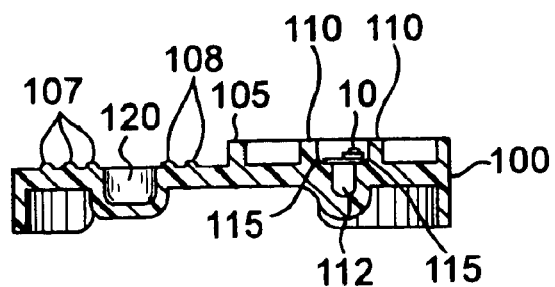
FIG. 6 is a cross-section view taken along line 6—6 of FIG. 5.

For the embodiment illustrated in FIGS. 1 to 6, the package 100 further includes a receptacle 120 for holding the device after removing it from the containment region. After removing the device, a surgeon may wish to temporarily set down the device, and receptacle 120 provides a convenient receptacle for doing so. Also, as explained in more detail below, the entire package 100 is preferably sterile, so receptacle 120 provides a sterile surface for placing the device. In the illustrated embodiment, after removing the device 10 from the containment region, the surgeon will add sutures to the suture tab 12 on the device, the sutures for suturing the device to eye tissue. FIG. 5, in addition to illustrating device in the containment region resting on pedestal surface 115, illustrates device 10 in receptacle 120 with the added sutures 13 resting on ribs 107, 108. The device may be held in receptacle 20 while the surgeon readies the eye for implantation of the device. In this embodiment, receptacle 120 has the form of a generally rectangular groove extending below surface 101 and located between ribs 107 and ribs 108.

Package 100 may be molded from a plastic such as polycarbonate, polypropylene or polystyrene. In packaging the device 10 in package 100, the device 10 is placed in the containment region of the package, and lidstock 20 is sealed against flange 105, so that the assembly assumes the configuration shown in FIG. 3. Then, the entire assembly is sterilized, for example, with heat. It is preferred that the assembly is then placed in a sterile pouch conventionally used to store surgical instruments.

Figure 7:
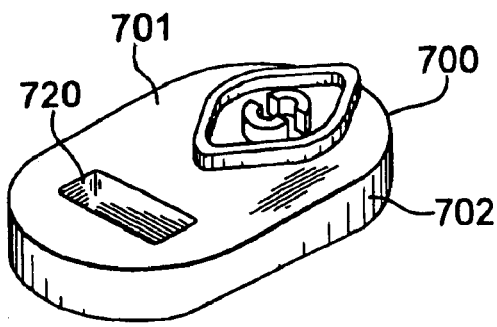
FIG. 7 is a top perspective view of a second package.

FIG. 7 illustrates an alternate embodiment of package 700. In this embodiment, the package 700 is supported on a work surface by a single vertical sidewall 702 extending downwardly from top planar surface 701. Also, this embodiment lacks ribs in the vicinity of receptacle 720.

Figure 8:
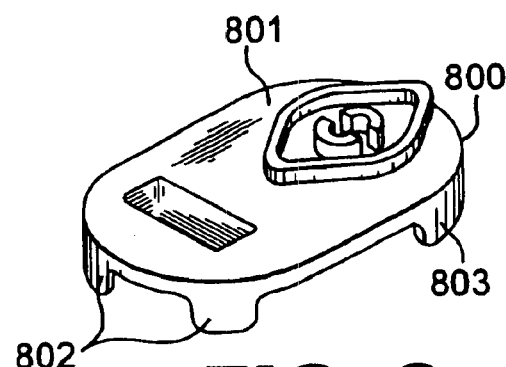
FIG. 8 is a top perspective view of a third package.

FIG. 8 illustrates another alternate embodiment of package 800. In this embodiment, the package 800 is supported on a work surface by front and rear legs 802, 803 extending downwardly from top planar surface 801.

Figure 9:
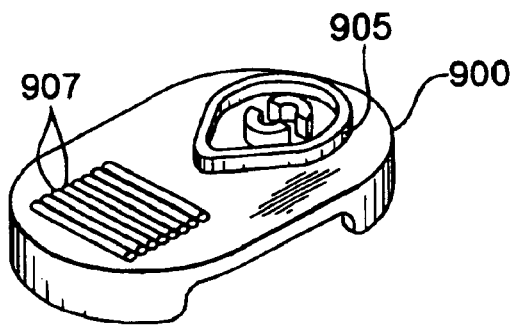
FIG. 9 is a top perspective view of a fourth package.

FIG. 9 illustrates an alternate embodiment of package 900. In this embodiment, the package 900 includes ribs 907 to facilitate a user steadying the package while removing lidstock, but lacks a holding receptacle in the vicinity of ribs 907. Also, this embodiment includes a chevron-shaped lidstock-sealing flange 905. For this embodiment, it would be recommended that a user remove lidstock by gripping the lidstock in the vicinity of the pointed end of the chevron-shaped flange and pulling the lidstock backward.

Figure 10:
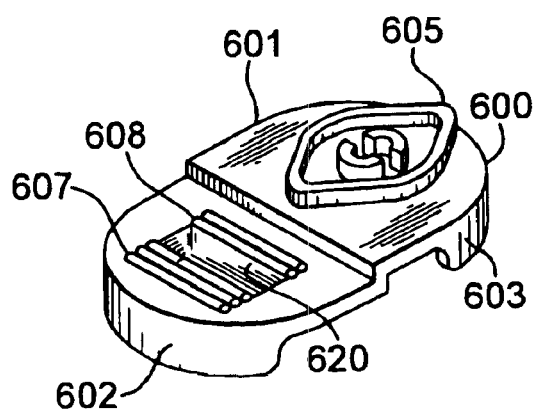
FIG. 10 is a top perspective view of a fifth package.

FIG. 10 illustrates an alternate embodiment of package 600. In this embodiment, the flange 605 and rear vertical wall 603 extend from a first planar surface 601, whereas holding receptacle 620, ribs 607, 608, and front vertical wall 602 extend from a second planar surface 630.

While the invention has been described with reference to various preferred embodiments, other alternate embodiments and variations will be evident to a person of ordinary skill in the art.

What is claimed:

1. A package for storing an implantable medical device during storage and shipping, comprising:

an upper surface;

a first flange extending upwardly from the upper surface and defining a containment region for containing the device, said containment region including a support surface for supporting the device in the containment region;

a second flange extending upwardly from the upper surface, said second flange surrounding the first flange and including an upper flange surface for sealing of lidstock thereto; and at least one side wall extending downwardly from the upper surface and serving to supporting the package on a work surface, further comprising a recess extending below the device support surface in the containment region, wherein the first flange comprises two protrusions extending upwardly from the upper surface and defining the containment region, and the recess has the form of an elongated groove separating the two protrusions and extending transversely to the containment region, wherein the two protrusions are arcuate, and wherein the maximum width between inner surfaces of an individual protrusion is 10 mm.

2. A package for storing an implantable medical device during storage and shipping, comprising:

an upper surface;

a first flange extending upwardly from the upper surface and defining a containment region for containing the device, said containment region including a support surface for supporting the device in the containment region;

a second flange extending upwardly from the upper surface, said second range surrounding the first flange and including an upper flange surface for sealing of lidstock thereto; and at least one side wall extending downwardly from the upper surface and serving to support the package on a work surface, further comprising a recess extending below the device support surface in the containment region, wherein the first flange comprises two protrusions extending upwardly from the upper surface and defining the containment region, and the recess has the form of an elongated groove separating the two protrusions and extending transversely to the containment region, wherein the two protrusions are arcuate, and wherein the maximum length between inner surfaces of the two protrusions is 10 mm, and the maximum width between inner surfaces of an individual protrusion is 5 mm.

3. An assembly comprising:

(a) a medical device implantable in the human eye;

(b) a package for storing the device during storage and shipping, comprising: an upper surface; a first flange extending upwardly from the upper surface and defining a containment region for containing the device, said containment region including a support surface for supporting the device in the containment region; and a second flange extending upwardly from the upper surface and completely surrounding the first flange; and (c) lidstock hermetically sealed to an upper surface of the second flange;

wherein the package further comprises at least one sidewall extending downwardly from the upper surface and serving to support the device on a work surface, and, wherein the package further comprises a holding receptacle separate from the containment region and not surrounded by the second flange.

* * * * *